(12) United States Patent
McGuckin, Jr.

(10) Patent No.: US 9,855,402 B2
(45) Date of Patent: Jan. 2, 2018

(54) APPARATUS FOR DELIVERING FLUID TO TREAT RENAL HYPERTENSION

(71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

(*) Notice: Subject to any disclaimer, the term of this patent is extended or adjusted under 35 U.S.C. 154(b) by 251 days.

(21) Appl. No.: 14/578,366

(22) Filed: Dec. 20, 2014

(65) Prior Publication Data

US 2015/0231372 A1 Aug. 20, 2015

Related U.S. Application Data

(60) Provisional application No. 61/940,404, filed on Feb. 15, 2014.

(51) Int. Cl.
*A61M 31/00* (2006.01)
*A61M 25/00* (2006.01)
(Continued)

(52) U.S. Cl.
CPC ..... *A61M 25/0084* (2013.01); *A61M 25/0082* (2013.01); *A61M 25/04* (2013.01);
(Continued)

(58) Field of Classification Search
CPC .... A61M 2025/0087; A61M 2025/105; A61M 2025/1052; A61M 25/0082; A61M 25/0084; A61M 25/04; A61M 25/10
See application file for complete search history.

(56) References Cited

U.S. PATENT DOCUMENTS

| 4,013,080 A | 3/1977 | Froning |
| RE31,873 E | 4/1985 | Howes |

(Continued)

FOREIGN PATENT DOCUMENTS

| CN | 2389625 | 8/1999 |
| WO | 9846119 | 10/1998 |

OTHER PUBLICATIONS

T.G. Frank, W. Xu and A. Cuschieri, "Instruments based on shape-memory allow properties for minimal access surgery, interventional radiology and flexible endoscopy", 2000 (4 pages).

(Continued)

*Primary Examiner* — Rebecca E Eisenberg
(74) *Attorney, Agent, or Firm* — Neil D. Gershon

(57) ABSTRACT

A surgical apparatus for delivering fluid to treat renal hypertension including an elongated member having a distal tip and a plurality of openings formed in a sidewall proximal of the distal tip. A plurality of fluid delivery members are movably positioned in the elongated member, each of the fluid delivery members having a lumen and at least one opening communicating with the lumen for delivering fluid extravascularly. An actuator is operatively associated with the fluid delivery members, the actuator actuable to a first position to move the fluid delivery members from a retracted position within the elongated member to a deployed position extending radially with respect to the elongated member. A balloon is expandable radially from the elongated member to seal the renal artery during application of fluid through the fluid delivery members.

12 Claims, 7 Drawing Sheets

(51) Int. Cl.
*A61M 25/04* (2006.01)
*A61M 25/10* (2013.01)

(52) U.S. Cl.
CPC .............. *A61M 2025/0087* (2013.01); *A61M 2025/1052* (2013.01)

(56) References Cited

U.S. PATENT DOCUMENTS

| | | |
|---|---|---|
| 4,645,491 A | 2/1987 | Evans |
| 4,760,847 A | 8/1988 | Vaillancourt |
| 4,769,005 A | 9/1988 | Ginsburg et al. |
| 4,808,157 A | 2/1989 | Coombs |
| 4,842,585 A | 6/1989 | Witt |
| 4,846,799 A | 7/1989 | Tanaka et al. |
| 4,869,259 A | 9/1989 | Elkins |
| 4,894,057 A | 1/1990 | Howes |
| 4,926,860 A | 5/1990 | Stice et al. |
| 4,958,901 A | 9/1990 | Coombs |
| 5,067,957 A | 11/1991 | Jervis |
| 5,102,396 A | 4/1992 | Bommarito |
| 5,139,485 A | 8/1992 | Smith et al. |
| 5,160,323 A | 11/1992 | Andrew |
| 5,195,526 A | 3/1993 | Michelson |
| 5,207,652 A | 5/1993 | Kay |
| 5,215,527 A | 6/1993 | Beck et al. |
| 5,231,989 A | 8/1993 | Middleman et al. |
| 5,236,424 A | 8/1993 | Imran |
| 5,242,448 A | 9/1993 | Pettine et al. |
| 5,275,611 A | 1/1994 | Behl |
| 5,354,279 A | 10/1994 | Hofling |
| 5,360,416 A | 11/1994 | Ausherman et al. |
| 5,385,148 A | 1/1995 | Lesh et al. |
| 5,385,544 A | 1/1995 | Edwards et al. |
| 5,403,311 A | 4/1995 | Abele et al. |
| 5,405,376 A | 4/1995 | Mulier et al. |
| 5,419,777 A | 5/1995 | Hofling |
| 5,431,649 A | 7/1995 | Mulier |
| 5,435,805 A | 7/1995 | Edwards et al. |
| 5,458,597 A | 10/1995 | Edwards et al. |
| 5,464,395 A | 11/1995 | Faxon et al. |
| 5,507,802 A | 4/1996 | Imran |
| 5,558,673 A | 9/1996 | Edwards et al. |
| 5,562,683 A | 10/1996 | Chan |
| 5,562,687 A | 10/1996 | Chan |
| 5,588,960 A | 12/1996 | Edwards et al. |
| 5,599,345 A | 2/1997 | Edwards et al. |
| 5,601,572 A | 2/1997 | Middleman et al. |
| 5,607,389 A | 3/1997 | Edwards et al. |
| 5,611,778 A | 3/1997 | Brinon |
| 5,620,419 A | 4/1997 | Lui et al. |
| 5,672,174 A | 9/1997 | Gough et al. |
| 5,683,384 A | 11/1997 | Gough et al. |
| 5,693,029 A | 12/1997 | Leonhardt |
| 5,713,853 A | 2/1998 | Clark et al. |
| 5,738,650 A | 4/1998 | Gregg |
| 5,795,318 A | 8/1998 | Wang et al. |
| 5,810,804 A | 9/1998 | Gough et al. |
| 5,827,276 A | 10/1998 | LeVeen et al. |
| 5,849,011 A | 12/1998 | Jones et al. |
| 5,855,576 A | 1/1999 | LeVeen et al. |
| 5,863,290 A | 1/1999 | Gough et al. |
| 5,873,865 A | 2/1999 | Horzewski et al. |
| 5,897,531 A | 4/1999 | Amirana |
| 5,951,547 A | 9/1999 | Gough et al. |
| 5,964,796 A | 10/1999 | Imran |
| 5,980,517 A | 11/1999 | Gough |
| 6,004,295 A | 12/1999 | Langer et al. |
| 6,009,877 A | 1/2000 | Edwards |
| 6,059,780 A | 5/2000 | Gough et al. |
| 6,074,367 A | 6/2000 | Hubbell |
| 6,080,150 A | 6/2000 | Gough |
| 6,102,887 A | 8/2000 | Altman |
| 6,106,521 A | 8/2000 | Blewett et al. |
| 6,129,726 A | 10/2000 | Edwards et al. |
| 6,132,425 A | 10/2000 | Gough |
| 6,159,196 A | 12/2000 | Ruiz |
| 6,179,813 B1 | 1/2001 | Ballow et al. |
| 6,190,353 B1 | 2/2001 | Makower et al. |
| 6,190,360 B1 | 2/2001 | Iancea et al. |
| 6,200,274 B1 | 3/2001 | McNeimey |
| 6,203,524 B1 | 3/2001 | Burney et al. |
| 6,217,554 B1 | 4/2001 | Green |
| 6,217,559 B1 | 4/2001 | Foster |
| 6,221,049 B1 | 4/2001 | Selmon et al. |
| 6,228,049 B1 | 5/2001 | Schroeder et al. |
| 6,231,591 B1 | 5/2001 | Desai |
| 6,254,573 B1 | 7/2001 | Haim et al. |
| 6,264,667 B1 | 7/2001 | McGuckin, Jr. |
| 6,280,424 B1 | 8/2001 | Chang et al. |
| 6,283,951 B1 | 9/2001 | Flaherty et al. |
| 6,302,870 B1 | 10/2001 | Jacobsen et al. |
| 6,306,141 B1 | 10/2001 | Jervis |
| 6,319,230 B1 | 11/2001 | Palasis et al. |
| 6,346,095 B1 | 2/2002 | Gross et al. |
| 6,425,887 B1 | 7/2002 | McGuckin et al. |
| 6,428,517 B1 | 8/2002 | Hochman et al. |
| 6,432,092 B2 | 8/2002 | Miller |
| 6,511,458 B2 | 1/2003 | Milo et al. |
| 6,730,061 B1 | 5/2004 | Cuschieri et al. |
| 6,905,480 B2 | 6/2005 | McGuckin et al. |
| 6,989,004 B2 | 1/2006 | Hinchliffe et al. |
| 7,087,040 B2 | 8/2006 | McGuckin et al. |
| 2002/0143302 A1* | 10/2002 | Hinchliffe .............. A61B 18/00 604/272 |
| 2008/0255642 A1* | 10/2008 | Zarins ................ A61B 18/1206 607/99 |
| 2012/0259216 A1* | 10/2012 | Gerrans ............. A61B 1/00165 600/435 |

OTHER PUBLICATIONS

Second Department of Internal Medicine, Faulty of Medicine, University of Tokyo, Japan, Gastroenterologia Japonica (Japan) Feb. 1991, p. 47-50, "Multiple-needle insertion method in Percutaneous ethanol injection therapy for liver neoplasms", Shiina S; Hta Y; Niwa Y; Komatsu Y; Tanaka T; Yoshiura K; Hamada E; Ohshima M; Mutoh H; Kurita M; et al.

* cited by examiner

APPARATUS FOR DELIVERING FLUID TO TREAT RENAL HYPERTENSION

This application claims the benefit of provisional application Ser. No. 61/940,404, filed Feb. 15, 2014, the entire contents of which are incorporated herein by reference.

BACKGROUND

Technical Field

This application relates to a surgical apparatus for delivering fluid and more particularly to an apparatus that delivers fluid to treat renal hypertension.

Background of Related Art

Renal hypertension consists of high blood pressure caused by the kidneys hormonal response to narrowing of the arteries supplying the kidneys. That is, when there is low blood flow, the kidneys respond by increasing blood pressure as the kidneys give off hormones that signal the body to retain salt and water, thereby causing a rise in blood pressure. Narrowing of the arteries is referred to as renal artery stenosis and can be caused by arterosclerosis or arterial injury. Hypertension can also be caused by hyperactive renal sympathetic nerves.

There are various treatments for renal hypertension. One treatment mode is the use of anti-hypertension drugs to modulate blood pressure. There are also surgical treatments. One surgical treatment is angioplasty, which can be accompanied by stent placement. However, restenosis often occurs. Other treatments include application of radiofrequency ablation to destroy the nerves within the renal artery with the objective of reducing blood pressure.

U.S. Pat. Nos. 8,339,443 and 8,465,752 disclose catheters advanced intravascularly. A needle is advanced through the blood vessel wall into adventitial tissue within a perivascular region. A neuromodulating agent is injected into the perivascular region to enhance concentrations of the agent in tissue surrounding the blood vessel, e.g., the renal artery, to apply directly to the area where nerve cells can be affected. By affecting, e.g., severing, the nerves, blood pressure can be reduced.

The need exists for an improved device for treating renal hypertension.

SUMMARY

The present invention advantageously provides a surgical apparatus for delivering fluid outside the vessel to treat renal hypertension. In accordance with one aspect of the present invention, an apparatus is provided comprising an elongated member having a distal tip and a plurality of openings formed in a sidewall proximal of the distal tip, a plurality of fluid delivery members movably positioned in the elongated member and having a lumen and at least one opening communicating with the lumen for delivering fluid extravascularly, and an actuator operatively associated with the fluid delivery members. The actuator is actuable to a first position to move the plurality of fluid delivery members from a retracted position within the elongated member to a deployed position extending radially with respect to the elongated member. A balloon is expandable to seal off the renal artery during fluid injection.

In some embodiments, the fluid delivery members exit the apparatus proximally of the balloon; in other embodiments, the fluid delivery members exit the apparatus distally of the balloon.

Preferably the distal tips of the fluid delivery members are sharp to penetrate a wall of the artery. The actuator is preferably axially slidable to move the fluid delivery members between the retracted and deployed position. In some embodiments, the distal tips of the fluid delivery members do not extend distally of the distal tip of the elongated member. The fluid delivery members can be composed of shape memory metal, or alternately, of stainless steel, or of other materials.

A retention member can be provided in the form of a tab mounted on the actuator that engages one of the recesses formed in a housing through which the actuator is slidably received. A visible indicator may be provided to indicate the position of the plurality of fluid delivery members.

In accordance with another aspect of the present invention, a method for treating renal hypertension is provided comprising:

inserting an apparatus intravascularly to a renal artery;

inflating a balloon on the apparatus to seal off the renal artery;

advancing an actuator in a first direction to deploy a plurality of tines radially through side openings in the apparatus so the tines penetrate a wall of the artery; and injecting fluid through a lumen in the tines and through side openings in the tines to apply ablation fluid outside the vessel wall.

In one embodiment, the plurality of tines are composed of shape memory material.

In some embodiments, a distal tip of the tines does not extend distally of a distal tip of the apparatus. In some embodiments, the tines exit the apparatus proximally of the balloon; in other embodiments, the tines exit the apparatus distally of the balloon.

BRIEF DESCRIPTION OF THE DRAWINGS

Preferred embodiment(s) of the present disclosure are described herein with reference to the drawings wherein:

FIG. 5 is a transverse cross-sectional view taken along line 5-5 of FIG. 3;

FIGS. 6-8 illustrate the insertion method for the apparatus of FIG. 1 to treat renal hypertension wherein FIG. 6 illustrates insertion of a guidewire through the femoral artery, FIG. 7 illustrates insertion of the apparatus of FIG. 1 over the guidewire and FIG. 8 illustrates inflation of the balloon to close off the renal artery;

DETAILED DESCRIPTION OF PREFERRED EMBODIMENTS

Figure 1:
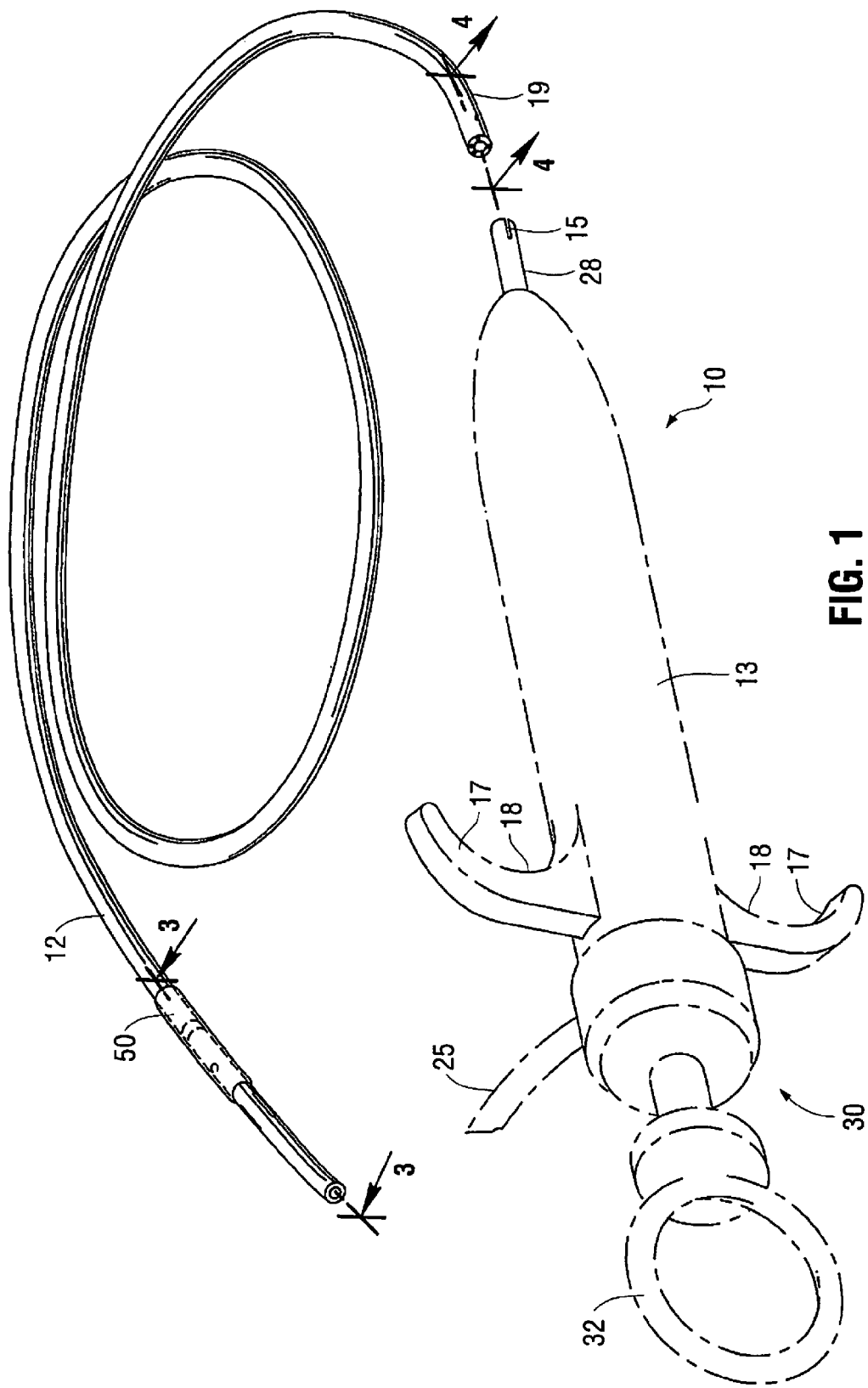
FIG. 1 is a perspective view of the surgical apparatus of the present invention, the fluid delivery members (tines) shown in the retracted position within the catheter.
Figure 2:
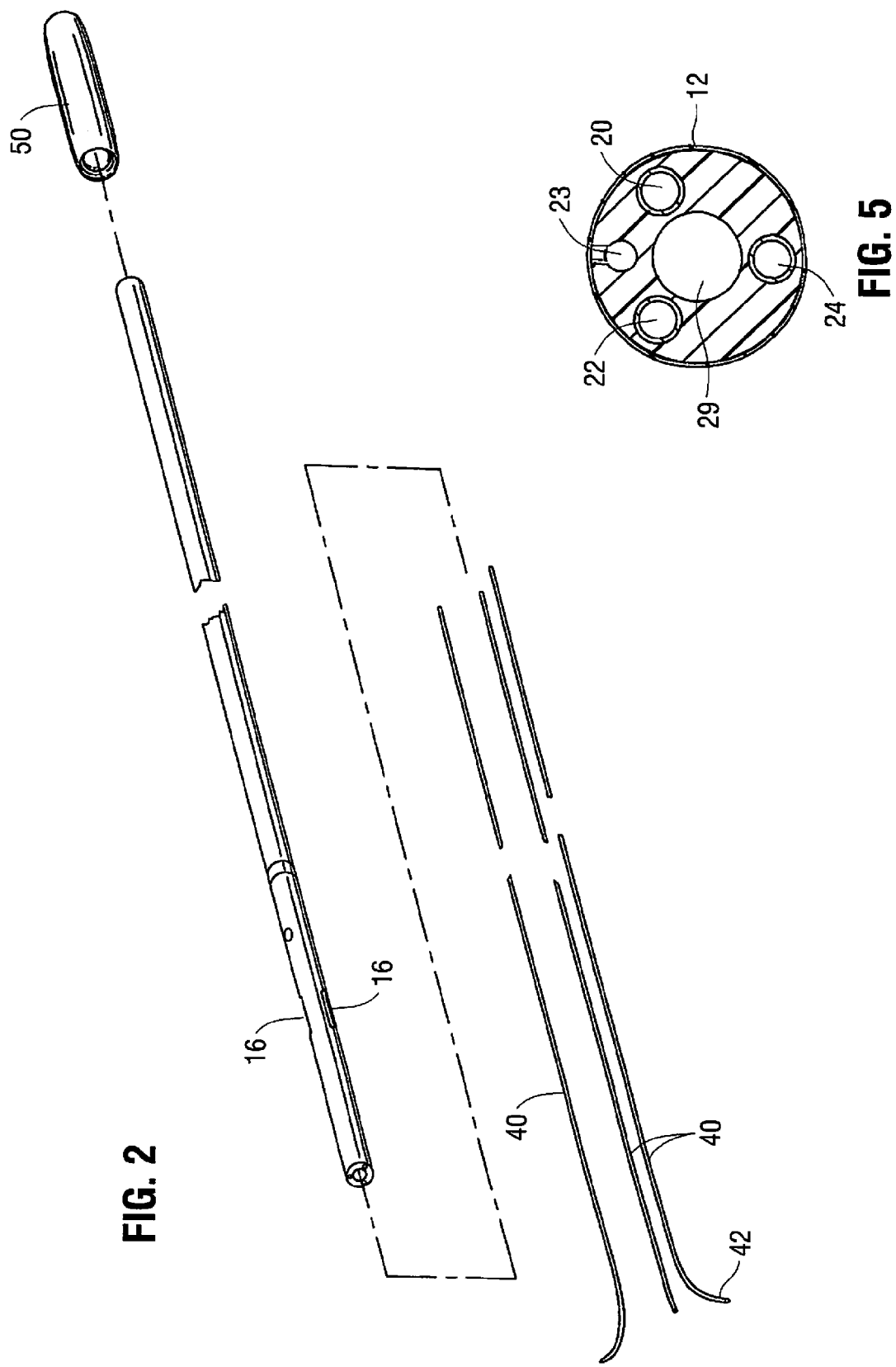
FIG. 2 is an exploded view of the catheter of FIG. 1.
Figure 3:
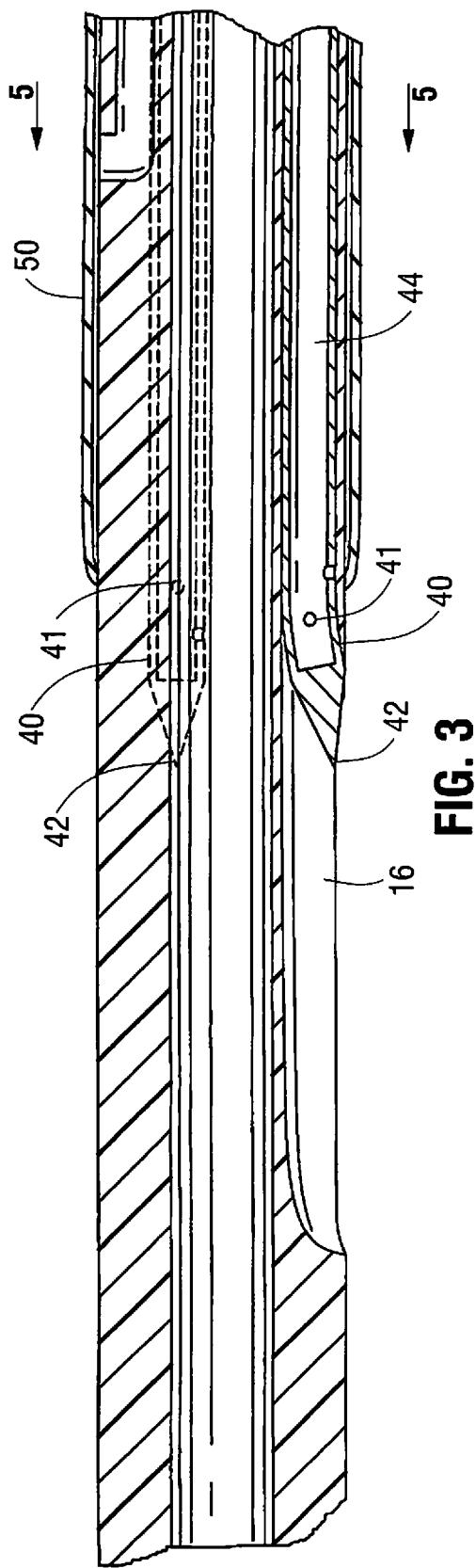
FIG. 3 is a longitudinal cross-sectional view taken along line 3-3 of FIG. 1.
Figure 4:
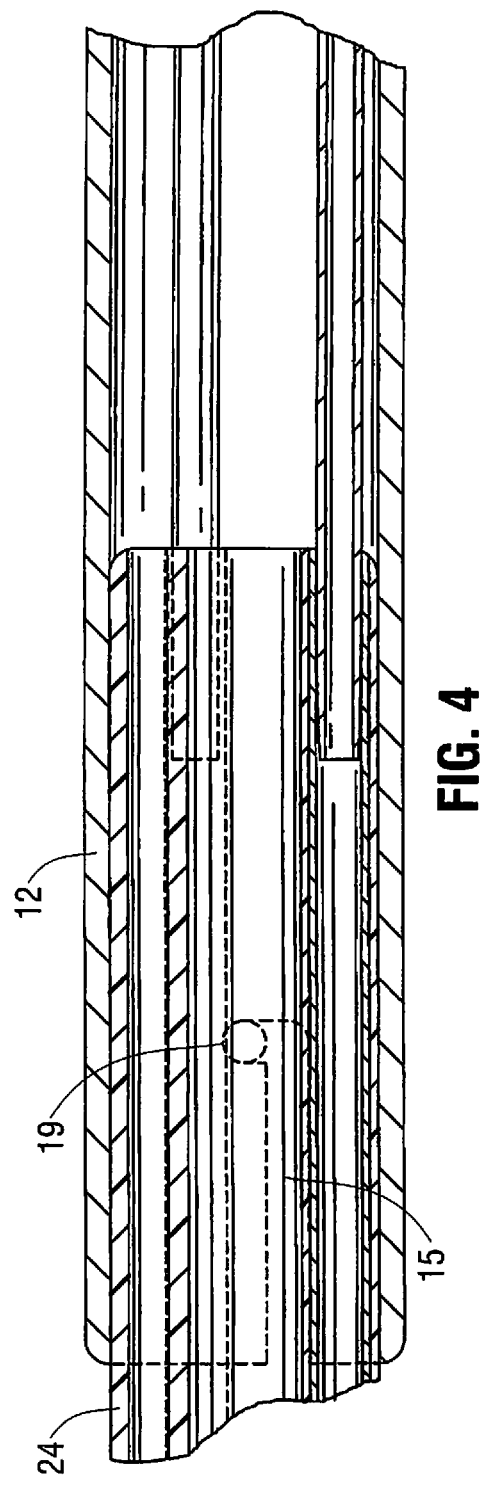
FIG. 4 is a longitudinal cross-sectional view taken along line 4-4 of FIG. 1.

Referring now in detail to the drawings where like reference numerals identify similar or like components throughout the several views, the apparatus of the present invention for delivering fluid for treatment of renal hypertension is designated generally by reference numeral 10 and illustrated in FIGS. 1 and 2. Apparatus 10 includes a flexible catheter or outer member (tube) 12, an actuator or plunger 30 extending proximally from housing 13, a plurality of fluid delivery members 40 and an expandable balloon 50. The fluid delivery members (tines) 40 are movable with respect to the outer member (tube) 12 in response to movement of the plunger 30 as the delivery members 40 are operably connected to plunger 30. The tines 40 include a lumen 44 in fluid communication with one or more side openings 41 for delivery of fluid to the target tissue and extend through respective side windows 16 in the outer member 12 (FIG. 3). In addition or as an alternative, the tines 40 can terminate in a distal opening to deliver fluid.

The tines 40 in one embodiment extend in their advanced position to a position proximal of the distal tip of the outer tube 12, thereby controlling the zone of fluid delivery. Since the tines in FIG. 1 are in the retracted position within the outer member 12, they are not visible in this Figure. The longitudinal cross-sectional view of FIG. 3 shows the tines 40 in their retracted position. The tines terminate in penetrating tips 42 to penetrate the vessel wall.

The housing 13 at the proximal end of the outer member 12 can be formed by two housing halves attached together. Wings 17 with finger recesses 18 facilitate gripping by the clinician.

A fluid port (not shown) can be provided to communicate with lumen 23 in catheter 12 to provide inflation fluid to inflate the balloon 50.

Plunger (actuator) 30 can optionally include finger ring 32 and is movable with respect to the housing from a retracted (proximal) position (FIG. 1) to an advanced (distal) position to deploy the tines 40 from the outer tube 12. An indicator (not shown) can be provided for visualization through a window on the housing 13 to indicate the position of the plunger 30 which in turn indicates the position of the tines 40 with respect to the elongated member 12.

Plunger 30 is shown in the initial position in FIGS. 1-3 which corresponds to the proximalmost position of the tines 40 in which they are retracted within outer tube 12 and their penetrating tips 42 are not exposed. The tines 40 can be connected at their proximal ends to a distal end of a connecting tube (described below) which is attached at its proximal end to a distal end of plunger 30 to effect movement of the tines 40. Alternatively, a proximal end of the tines 40 can be attached to a distal end of the plunger 30 and the connecting tube described below positioned within the plunger 30.

Catheter 12 has three longitudinally extending lumens 20, 22, 24 (see FIG. 5) configured and dimensioned to enable sliding movement of the tines 40 between retracted and advanced (extended) positions. Central lumen 29 is configured to receive a guidewire for over the wire insertion of the catheter 12.

Catheter 12 in one embodiment is mounted to housing 13 by pin 19 extending into receiving groove 15, although other attachments are contemplated. The attachment can be done during manufacture or alternatively done by the clinician after the apparatus packaging is opened.

An inner connecting tube is provided within housing 13, communicating with fluid source tube 25 having a lumen formed therein to accommodate fluid flow. Attachment tube 28 extends distally from housing 13 and is coupled to a proximal region of the outer tube 12. Inner connecting tube provides fluid to the tines 40 from source tube 25 to provide fluid communication between the lumen of connecting tube and the lumen of each tine 40.

The inner connecting tube can be composed of metal and have a flattened (swaged) region to help prevent rotation of the inner tube. The tines (fluid delivery members) 40 can be attached to the distal end of the inner tube, preferably by crimping or potting, so that axial movement of the inner tube moves the tines axially. Glue or solder may further be used at the attachment to seal the connection to the tines 40 to prevent fluid leakage. The inner tube is in fluid communication with the lumens in the tines 40 to deliver fluid received from the source tube 25.

Turning now to the tines (fluid delivery members) 40 of apparatus 10, in a preferred embodiment, three curved tines are provided, configured to extend radially with respect to the longitudinal axis of the outer member 12. A fewer or greater number of tines is also contemplated. Each of the tines 40 has a lumen 44, one or more openings 41 in the side wall in fluid communication with the lumen 44 of the tine, and a distal tip 42 for penetrating the vessel wall. In some embodiments, each of the tines has four side openings communicating with the tine lumen for delivering fluid to the tissue. In the embodiment where three tines 40 are provided, the tines are about 120 degrees apart. Note that a fewer or more side openings can be provided on various portions of one or more of the tines to communicate with the lumen to achieve the desired effect.

With reference to FIG. 3, in the initial position, tines 40 are positioned proximal of their respective sidewall openings 16 formed in outer tube 12 and are in a substantially straight position substantially parallel with the longitudinal axis of the needle tube 12.

Tines 40 can be composed of shape memory material, such as a nickel titanium alloy, and when in the retracted position are in a substantially straightened position within the outer member 12. When the tines 40 are deployed, the tines 40 extend through respective side openings 16 formed in the sidewall of the outer member 12 to assume a curved configuration such as that shown in FIG. 9. The tines 40 can be extended to various distances from outer member 12 and retained at such distances by a retention feature.

Note that in an alternate embodiment, stainless steel curved tines can be utilized. The stainless steel curved tines would move to a curved position when deployed.

Plunger 30 is advanced (slid) distally axially towards the housing 13, advancing the inner tube to distally to advance tines 40 through the respective side openings 16 of the outer member 12, enabling the tines 40 to extend angularly with respect to the longitudinal axis of the outer tube.

As illustrated, tines 40 remain proximal of the distal tip of outer member 12 in the deployed positions. This better controls the zone of tissue treatment. This is a result of the fact that when the tines 40 are deployed, the surgeon can be assured that the tines remain proximal of the distal edge of the catheter. However, it is also contemplated that the tines extend beyond the distal edge of the catheter.

Figure 6:
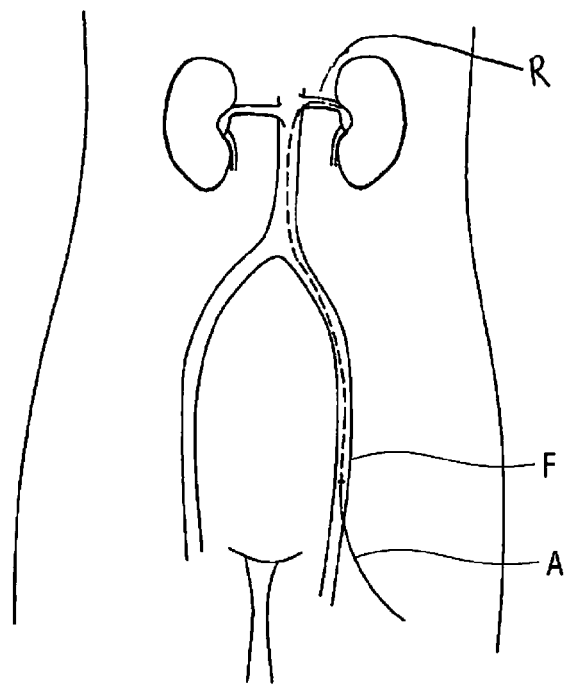
Figure 7:
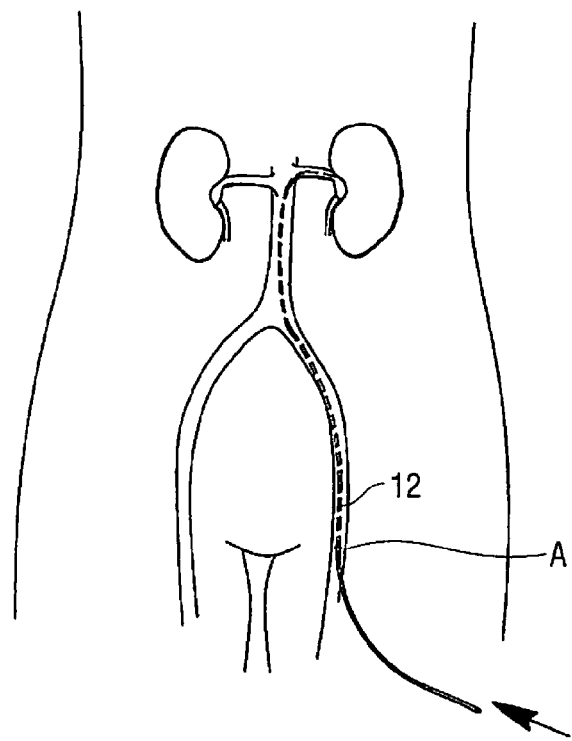
Figure 8:
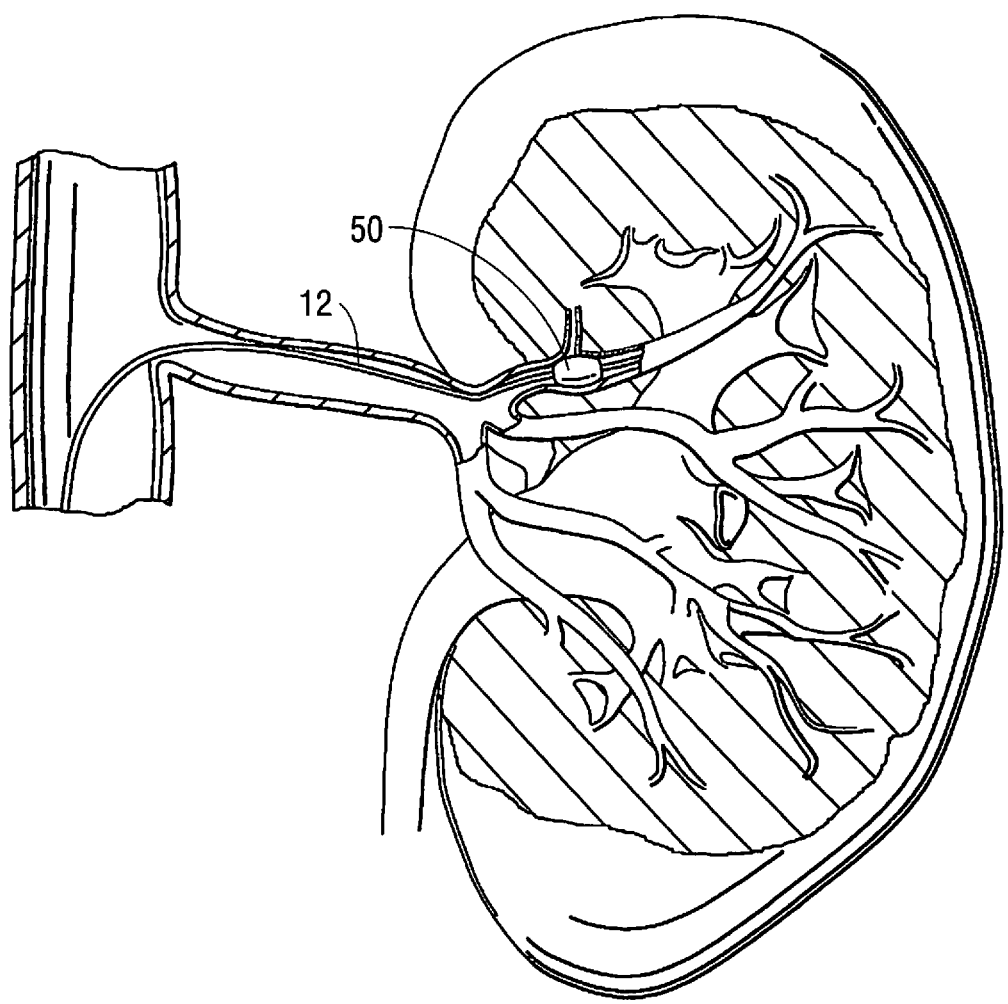
Figure 9:
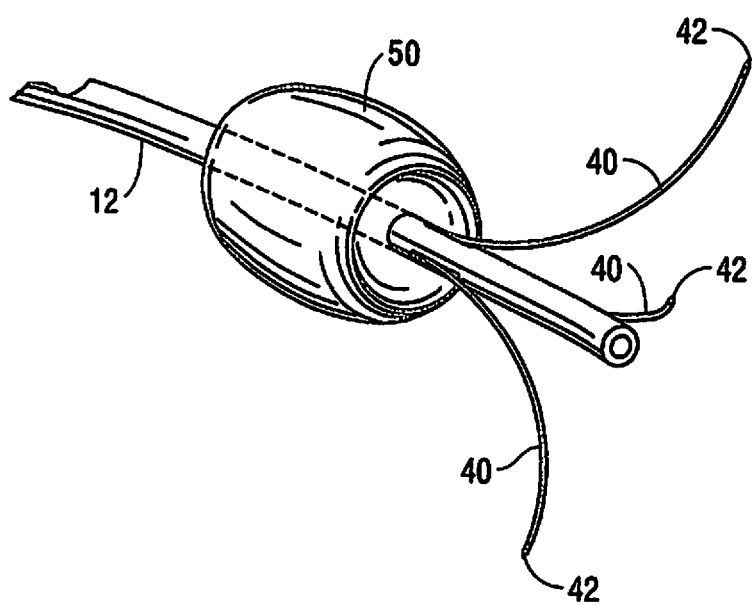
FIG. 9 is a perspective view of the balloon/tine region of the apparatus of FIG. 1 showing the tines exiting distally of the balloon.

In use, the apparatus 10 is inserted intravascularly to the target tissue site as shown in FIGS. 6-8. More specifically, the catheter is advanced over a guidewire A which is inserted through the femoral artery F and advanced intravascularly to the renal artery R. The guidewire A extends through the central lumen 29 of the catheter 12. The apparatus 10 is inserted with plunger 30 in the initial retracted position so that tines 40 are fully retracted inside outer tube 12 as shown in FIG. 1. The balloon 50 is then inflated to seal off the renal artery as shown in FIG. 8. Plunger 30 is pushed axially inwardly to deploy the tines 40 as shown in FIG. 9, with the penetrating tips 42 penetrating the vessel wall to apply ablation fluid intravascularly, thereby ablating nerves to treat renal hypertension. As noted above, an indicator can be provided to indicate to the user that the plunger 30 has been moved from its initial position. Note, alternatively, the balloon 50 can be inflated after the plunger 30 deploys the tines 40 (but before application of ablation fluid).

Figure 10:
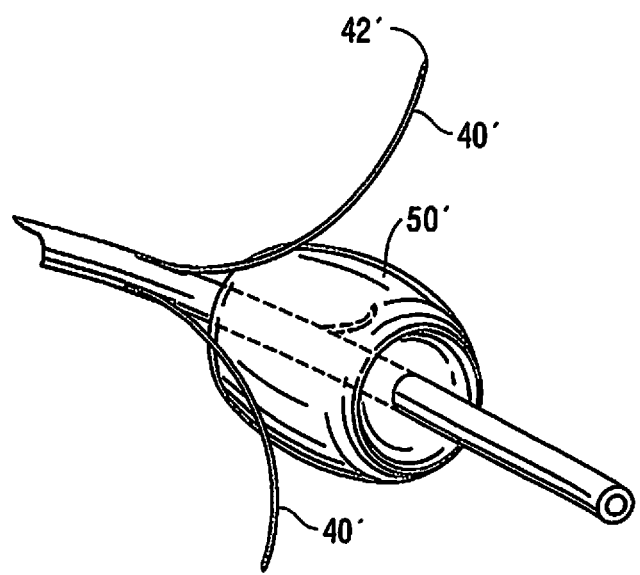
FIG. 10 is a perspective view of the balloon/tine region of an alternate embodiment of the apparatus of the present invention showing the tines exiting proximally of the balloon.

Next, ablation fluid is injected through source tube 25 which flows through the inner tube and through the lumens in tines 40, exiting through holes 41 in tines 40. As shown in FIG. 9, the tines exit distal of the balloon 50. However, in the alternate embodiment of FIG. 10, the tines 40' exit proximally of the balloon 50' and their penetrating tips 42' can in some embodiments remain proximal of the distal end of balloon 50'. In all other respects, tines 40' and the apparatus of FIG. 10 are identical to tines 40 and apparatus 10 of FIG. 1. In the deployed position, tines 40 (and tines 40') extend outwardly at an angle to the longitudinal axis, as they return to their memorized configuration.

Figure 8A:
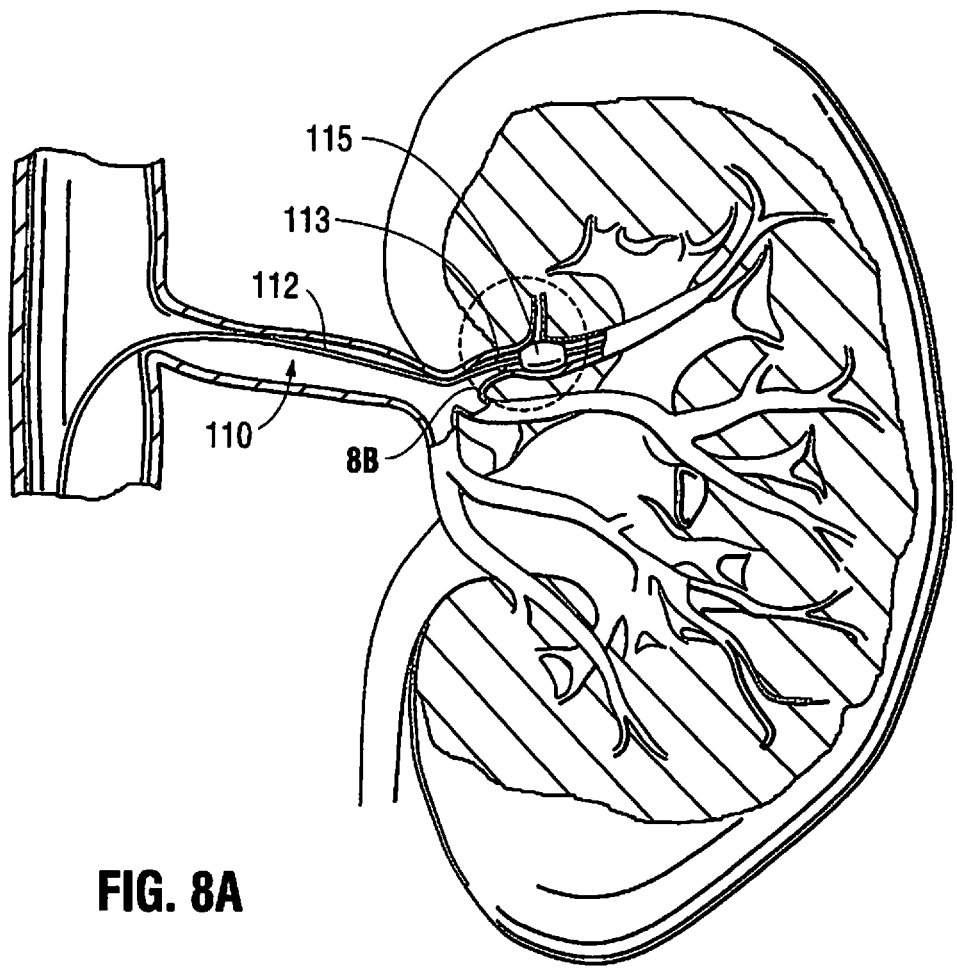
FIG. 8A is a view similar to FIG. 8 except showing an alternate embodiment of the apparatus having centering wires.
Figure 8B:
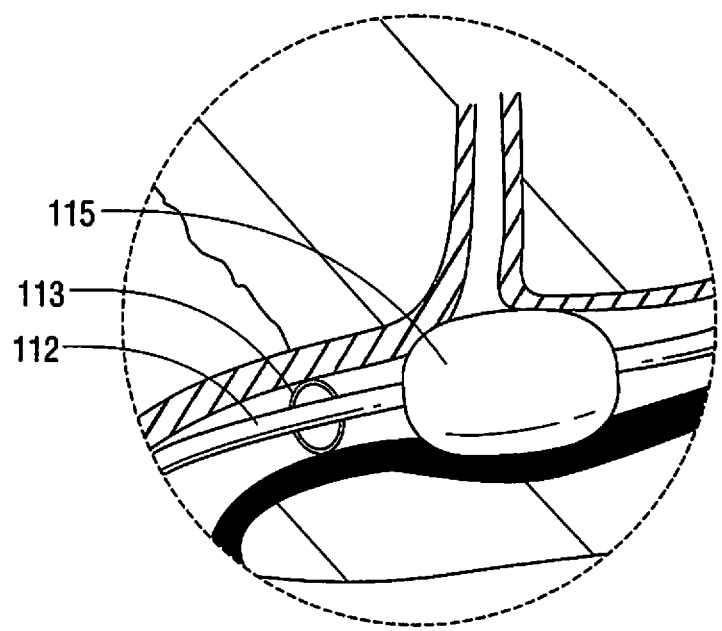
FIG. 8B is a close up view of the circled area of FIG. 8A.

In the alternate embodiment of FIG. 8A, catheter 112' is identical to catheter 12 of FIG. 1 except for the provision of centering structure 113. Centering structure 113 can be in the form of a plurality of wires arranged in a basket-like structure and in the expanded position center the catheter 112 within the vessel. The centering structure can be positioned proximal of the balloon 115 as shown in FIG. 8A, or alternatively, positioned distal of the balloon 115. The centering wires are in the collapsed insertion position and when exposed from the introducer automatically move to the expanded basket-like configuration. Two or more wires can be provided to form the centering structure. The wires can be made of shape memory material. Catheter 112 is part of apparatus 110 which is otherwise identical to apparatus 10, e.g., includes a plunger, inner tube for fluid delivery, tines, etc.

Although contemplated for treating renal hypertension, it is also contemplated that the apparatus can be utilized to deliver fluid and treat other regions of the body.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical apparatus for delivering fluid to treat renal hypertension comprising:

an elongated member having a distal tip and a plurality of openings formed in a sidewall proximal of the distal tip;

a plurality of fluid delivery members movably positioned in the elongated member, each of the fluid delivery members having a lumen and at least one opening communicating with the lumen for delivering fluid extravascularly to ablate nerves to reduce blood pressure to treat renal hypertension;

an actuator operatively associated with the fluid delivery members, the actuator actuable to a first position to move the fluid delivery members from a retracted position within the elongated member to a deployed position extending through the openings in the sidewall and radially with respect to the elongated member;

a balloon expandable radially with respect to the elongated member to seal a renal artery during application of fluid through the fluid delivery members, the renal artery sealed distal of a division of the renal artery; and an expandable centering wire basket structure positioned proximal of the balloon to center the apparatus.

2. The apparatus of claim 1, wherein the plurality of fluid delivery members are retained in the elongated member in a substantially straight position.

3. The apparatus of claim 1, wherein the plurality of fluid delivery members has a sharp tip configured to penetrate a wall of the artery.

4. The apparatus of claim 1, wherein the actuator is axially slidable to move the plurality of fluid delivery members between the retracted and deployed positions.

5. The apparatus of claim 1, wherein in the deployed position, a distal end of the fluid delivery members does not extend distally of the distal tip of the elongated member.

6. The apparatus of claim 1, wherein the plurality of fluid delivery members are composed of shape memory metal.

7. The apparatus of claim 1, wherein the openings formed in the sidewall of the elongated member are positioned proximal of the balloon and the plurality of fluid delivery members exit proximally of the balloon.

8. The apparatus of claim 1, wherein the openings formed in the sidewall of the elongated member are positioned distal of the balloon and the plurality of fluid delivery members exit distally of the balloon.

9. The apparatus of claim 1, further comprising a support tube slidably mounted within the elongated member and operatively connected to the actuator, the plurality of fluid delivery members connected to the support tube.

10. The apparatus of claim 1, wherein the at least one opening in the fluid delivery members is formed in a sidewall of the fluid delivery member.

11. The apparatus of claim 10, wherein the least one opening in the fluid delivery members includes multiple openings in the sidewall.

12. The apparatus of claim 1, wherein the elongated member includes a lumen dimensioned for insertion over a guidewire.

\* \* \* \* \*